(12) United States Patent
Dudenhoefer et al.

(10) Patent No.: US 9,433,939 B2
(45) Date of Patent: Sep. 6, 2016

(54) LIQUID DISPENSING ASSEMBLY FRAME

(75) Inventors: Christie Dudenhoefer, Corvallis, OR (US); Jeffrey A. Nielsen, Corvallis, OR (US); Kenneth Ward, Corvallis, OR (US); Kevin F. Peters, Corvallis, OR (US); Joseph W. Dody, Corvallis, OR (US); Alexander Govyadinov, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 569 days.

(21) Appl. No.: 12/870,546

(22) Filed: Aug. 27, 2010

(65) Prior Publication Data

US 2012/0051984 A1 Mar. 1, 2012

(51) Int. Cl.
| | |
|---|---|
| *B01L 3/00* | (2006.01) |
| *G01N 1/00* | (2006.01) |
| *G01N 21/00* | (2006.01) |
| *G01N 21/47* | (2006.01) |
| *B41J 2/135* | (2006.01) |
| *B01L 3/02* | (2006.01) |
| *B41J 2/045* | (2006.01) |
| *G01N 21/51* | (2006.01) |
| *B41J 2/21* | (2006.01) |
| *G01N 35/10* | (2006.01) |

(52) U.S. Cl.
CPC .......... *B01L 3/0268* (2013.01); *B41J 2/04561* (2013.01); *G01N 21/51* (2013.01); *B01L 2200/061* (2013.01); *B01L 2200/0642* (2013.01); *B01L 2200/143* (2013.01); *B01L 2400/02* (2013.01); *B41J 2/0451* (2013.01); *B41J 2/2142* (2013.01); *G01N 35/1016* (2013.01); *G01N 2021/513* (2013.01); *Y10T 436/25* (2015.01)

(58) Field of Classification Search
CPC .. B41J 2/14024; B41J 2/175; B41J 2/04561; B41J 2/1752; B41J 2/14072
See application file for complete search history.

(56) References Cited

U.S. PATENT DOCUMENTS

| | | | | |
|---|---|---|---|---|
| 4,940,998 | A | * | 7/1990 | Asakawa .......................... 347/37 |
| 5,877,580 | A | | 3/1999 | Swierkowski |
| 5,940,099 | A | * | 8/1999 | Karlinski ........................ 347/70 |
| 6,068,367 | A | | 5/2000 | Fabbri |
| 6,431,673 | B1 | | 8/2002 | Heim et al. |
| 6,460,964 | B2 | | 10/2002 | Osborne |
| 6,710,878 | B1 | * | 3/2004 | Dean et al. ................... 356/436 |
| 7,138,254 | B2 | | 11/2006 | Jovanovich et al. |
| 7,707,964 | B2 | | 5/2010 | Childers |
| 7,819,847 | B2 | | 10/2010 | Vitello et al. |
| 8,215,262 | B2 | | 7/2012 | Ishikawa et al. |
| 2002/0089561 | A1 | | 7/2002 | Weitzel et al. |

(Continued)

FOREIGN PATENT DOCUMENTS

| | | |
|---|---|---|
| EP | 1859870 | 11/2007 |
| JP | 8201394 A | 8/1996 |
| WO | 2009070540 A1 | 6/2009 |

*Primary Examiner* — P. Kathryn Wright
(74) *Attorney, Agent, or Firm* — HP Inc. Patent Department

(57) ABSTRACT

Various techniques for dispensing liquids are disclosed herein. In one embodiment a dispenser retention apparatus includes a frame. The frame includes a top surface configured to retain a liquid dispensing assembly. The frame also includes a bottom surface opposite the top surface. The bottom surface includes a first channel extending from a first lateral edge of the frame to a droplet passage between the top and bottom surfaces. The first channel is configured to allow a light beam introduced to the frame at the first lateral edge to intersect a droplet in the passage.

17 Claims, 7 Drawing Sheets

(56) References Cited

U.S. PATENT DOCUMENTS

| | | |
|---|---|---|
| 2002/0121529 A1 | 9/2002 | Hoummady |
| 2002/0140770 A1 | 10/2002 | Silverbrook et al. |
| 2002/0140776 A1 | 10/2002 | Silverbrook et al. |
| 2002/0140777 A1 | 10/2002 | Silverbrook et al. |
| 2002/0191049 A1 | 12/2002 | Silverbrook |
| 2003/0086828 A1* | 5/2003 | Chiou et al. ............... 422/100 |
| 2003/0137554 A1 | 7/2003 | Silverbrook et al. |
| 2004/0036726 A1 | 2/2004 | Zach |
| 2004/0254527 A1* | 12/2004 | Vitello et al. ............... 604/82 |
| 2006/0139405 A1* | 6/2006 | Nellen ....................... 347/49 |
| 2007/0111322 A1 | 5/2007 | Yang |
| 2008/0170089 A1 | 7/2008 | Albertalli et al. |
| 2009/0088336 A1 | 4/2009 | Burd et al. |
| 2009/0124015 A1 | 5/2009 | Dussi et al. |
| 2009/0244151 A1* | 10/2009 | Hendricks et al. ......... 347/14 |
| 2010/0265287 A1* | 10/2010 | Govyadinov et al. ...... 347/9 |
| 2012/0051984 A1 | 3/2012 | Dudenhoefer et al. |

* cited by examiner

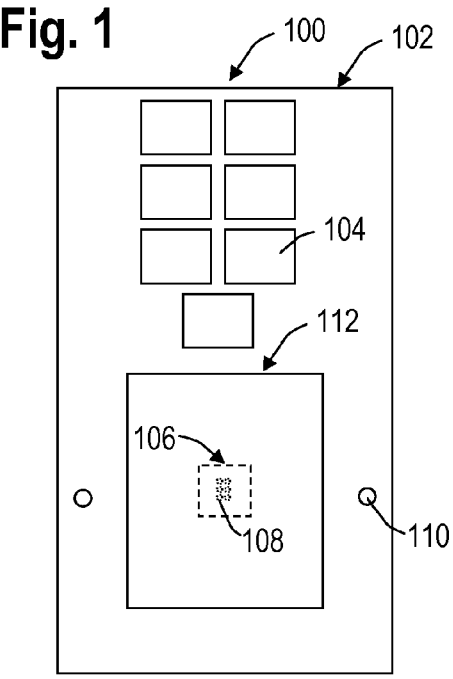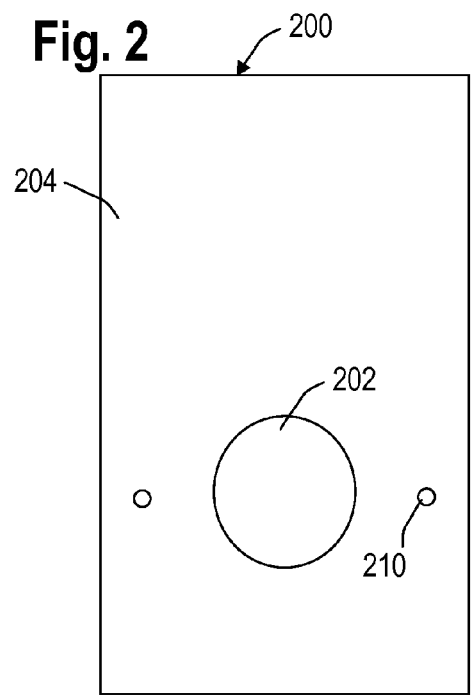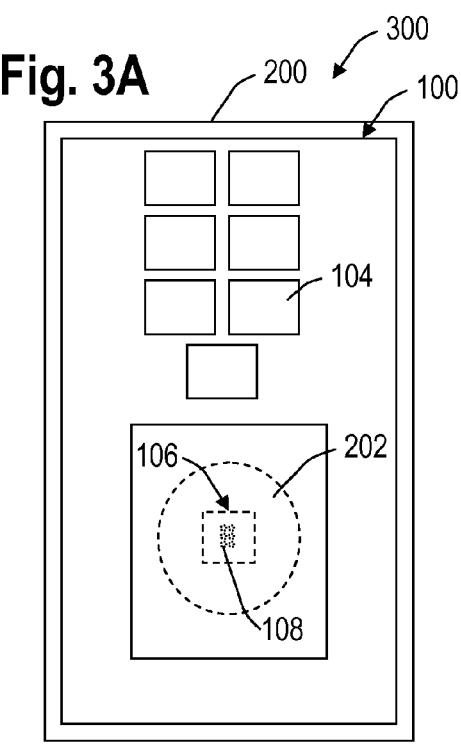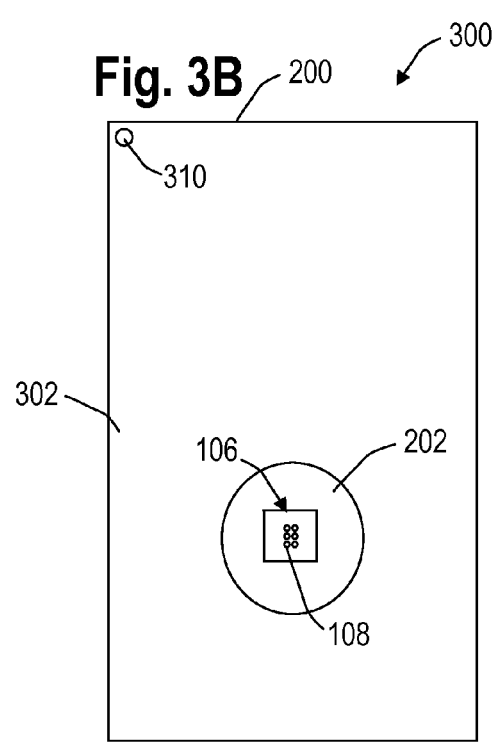

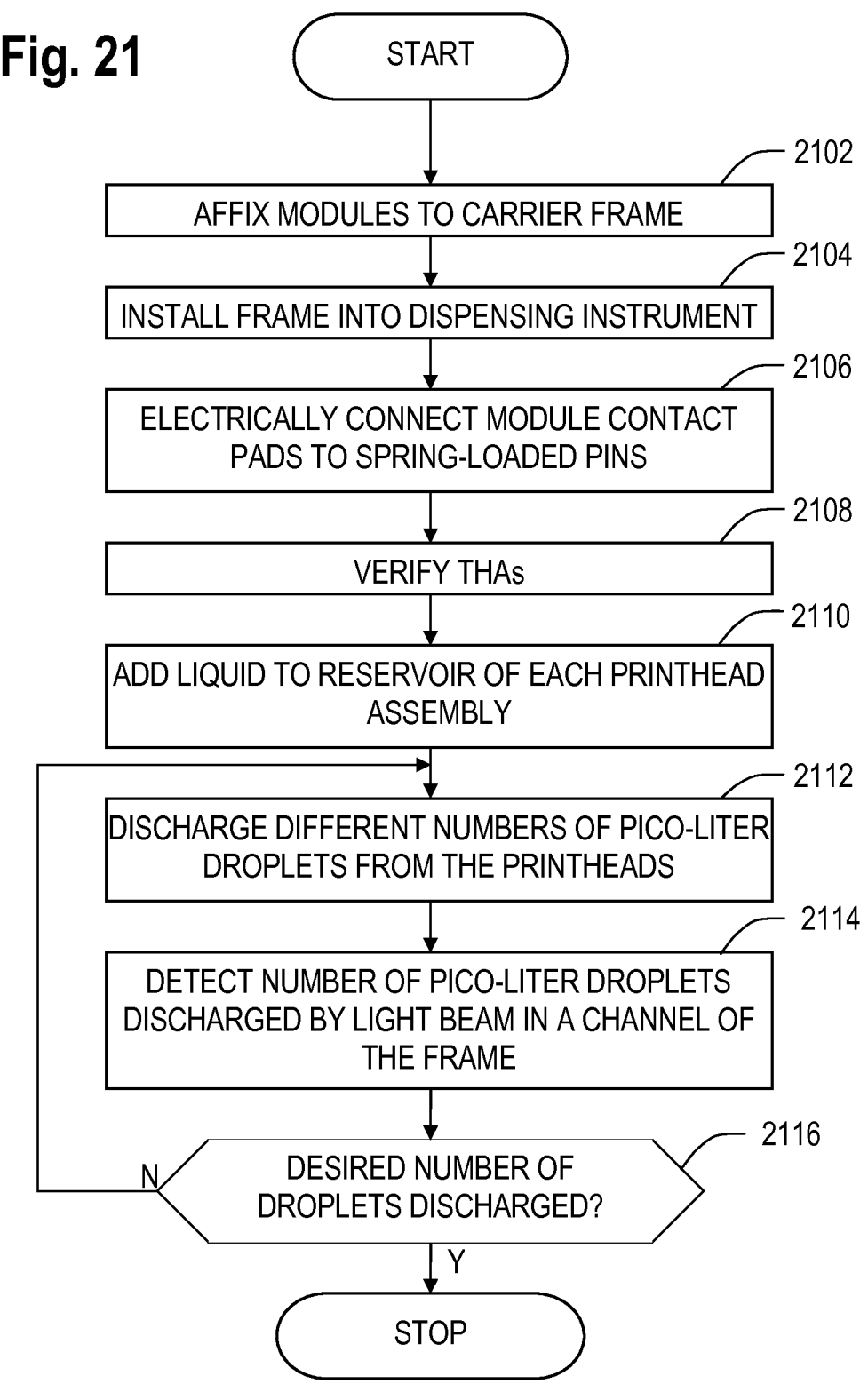

LIQUID DISPENSING ASSEMBLY FRAME

BACKGROUND

Dispensing of liquids in volumes from picoliters to microliters is an essential operation in many areas of pharmaceutical and biology research, as well as in medical and veterinary diagnostics, forensics testing, and agricultural testing. Even within these fields, low-volume liquid dispensing is used for many different operations.

One stage of pharmaceutical research, during which low-volume liquid dispensing is important, is directed to determining the concentration of a compound needed to effectively attack or inhibit a target (e.g., a virus). Many different concentrations of the compound are created in containers, such as the wells of a microplate (also known as a "well plate") to determine the effective concentration. Dispensing systems direct liquids into the wells. Serial dilution is applied to achieve a required concentration when the dispensing system is incapable of providing sufficiently small volumes of the compound.

BRIEF DESCRIPTION OF THE DRAWINGS

For a detailed description of exemplary embodiments of the invention, reference will now be made to the accompanying drawings in which:

FIG. 1 shows a top view of a head assembly in accordance with various embodiments;

FIG. 2 shows a top view of a frame configured to support a head assembly in accordance with various embodiments; and FIGS. 3A and 3B show top and bottom views of a head assembly module in accordance with various embodiments;

FIG. 21 shows a flow diagram for a method of titration in accordance with various embodiments.

NOTATION AND NOMENCLATURE

Figure 4:
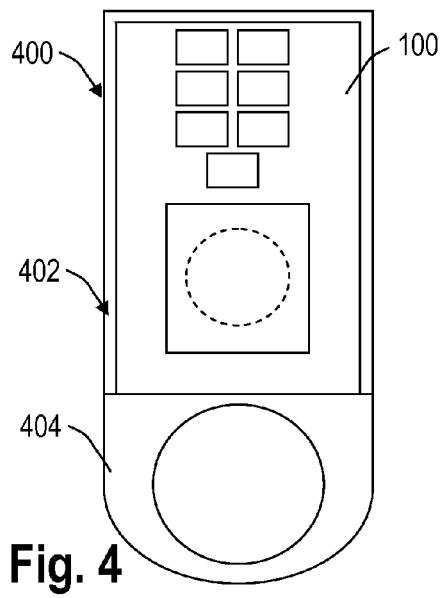
FIGS. 4 and 5 show a top view of a head assembly module including a handling feature in accordance with various embodiments.

Certain terms are used throughout the following description and claims to refer to particular system components. As one skilled in the art will appreciate, computer companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect, direct, optical or wireless electrical connection. Thus, if a first device couples to a second device, that connection may be through a direct electrical connection, through an indirect electrical connection via other devices and connections, through an optical electrical connection, or through a wireless electrical connection.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

One stage of pharmaceutical research is directed to determining the concentration of a compound needed to effectively attack a target (e.g., a virus). To determine an effective concentration of a compound, many different concentrations of the compound are created in trays of miniature test tubes called "well plates." A dispensing system distributes the compound into the well. If the dispensing system is unable to dispense sufficiently small volumes of the compound, serial dilution is applied to achieve a desired concentration.

Disclosed herein are techniques for using a frame conveying one or more liquid dispensing assemblies (e.g., titration head assemblies ("THA")) to dispense small volumes (e.g., pico-liters) of liquid very quickly. Such techniques provide a method to titrate solutions across many orders of magnitude of concentration without serial dilution. Those same techniques can be used to dispense low-volumes of a wide-variety of liquids containing active biological ingredients, assay components, markers, tags, or a wide variety of other fluids relevant to the fields of pharmaceutical research, bio research, forensics study, veterinary research and diagnostics, and medical diagnostics, to name a few. Embodiments of the frame may include one or two-dimensional arrays of THAs spaced in accordance with the wells of a microplate. Frame embodiments can also include multiple THA designs for dispensing a variety of fluids into many bioassay and other applications requiring similar technology.

Embodiments of the frame also include channels formed in the bottom surface of the frame. The channels improve the accuracy of light scattering drop detection by reducing the distance between dispenser nozzles a light beam passing below the nozzles, thereby permitting laser light to pass through and not be reflected, and enabling use of a higher numerical aperture fiber.

In some embodiments, THAs are rigidly attached to a frame with a solid bottom surface, and/or the frame includes features for ease and stability of stacking the frames, and/or the frame includes numbers for each THA or other human or machine readable ID marks on the frames to denote each THA or features of the frame or THAs.

FIG. 1 shows a top view of a THA 100 in accordance with various embodiments. The THA 100 includes a flexible substrate 102 (e.g., polyimide), electrical contact pads 104, a liquid reservoir 112, and a printhead 106 including an array of nozzles 108. The THA 100 may also include an alignment mark, for example, fiducials 110 for aligning the THA on a frame. The THA also includes conductive traces between the pads 104 and the printhead 106.

The printhead 106 may be based on, for example, thermal inkjet technology, or any other liquid dispensing technology capable of producing a desired droplet size. Embodiments of the printhead 106 may differ as to the number of nozzles 108, distribution of the nozzles 108, the type of fluid accommodated by the printhead 106 fluid chamber (e.g., aqueous, dimethyl sulfoxide, etc.), droplet volume, etc. With regard to droplet volume for example, one embodiment of the printhead 106 discharges 1-pico-liter droplets, another embodiment discharges 10-pico-liter droplets, and yet another embodiment discharges 100-pico-liter droplets. Similarly, embodiments of the THA 100 may include different liquid reservoirs 112 capable of holding different volumes of liquid (e.g., a 5 micro-liter reservoirs 112, a 50 micro-liter reservoirs receptacles 112, etc).

FIG. 2 shows a top view of frame 200 configured to support a titration head assembly 100 in accordance with various embodiments. The upper surface of the frame 200 is non-conductive in some embodiments to allow the titration head assembly 100 to be bonded to the frame 200 without shorting conductors of the THA 100. The frame 200 may be formed of a polymer material or may be metal or ceramic. A metallic frame may include a non-conductive coating in some areas to prevent the conductors of the THA 100 from shorting. An opening 202 is disposed in the frame 200 to allow droplets produced by the printhead 106 to pass through the frame 200. The frame 200 may also include alignment features 210 that guide placement of the THA 100 on the frame 100. The frame 200 is rigid enough to maintain its shape when electrical connections are made with the pads 104 via spring-loaded pins or another electrical connection method.

FIG. 3A shows a top view of a THA module 300 in accordance with various embodiments. The THA module 300 includes a THA 100 mounted onto a frame 200. The THA 100 may be bonded to the frame 200 by an adhesive. The THA 100 is aligned and secured to the frame 200 such that the nozzles 108 face into the opening 202 of the frame 200. The frame 200 provides support for the electrical contact pads 104 allowing electrical connections to be made with the pads 104 via spring-loaded pins when the frame is positioned in a dispensing instrument. The bottom surface 302 of the frame 300 may extend no more than 2 millimeters ("mm") (e.g., 0.50-2 mm in some embodiments) below the printhead 106, in some embodiments, to provide small printhead to drop receptacle spacing.

The frame 200 provides a reference for positioning the THA 100 for use. For example, by positioning the frame 200 relative to a receptacle intended to receive liquid from the THA 100, and/or a liquid delivery system configured to load the reservoir 112, the reservoir 112, printhead 106, pads 104, etc. are positioned for proper operation. By affixing the THA 100 to the rigid frame 200, the orientation of the THA 100 (e.g., horizontality of the printhead 106 and/or reservoir 112) can be controlled by controlling the orientation of the frame 200.

FIG. 3B shows a bottom view of the THA module 300 in accordance with various embodiments. The THA module 300 may include alignment features 310 allowing the module 300 to be properly positioned in a dispensing instrument and/or relative to a container positioned to receive liquid from the module 300. In some embodiments, the module 300 may be 9 mm or less in width and/or 25 mm or less in length. In some embodiments, the module 300 may be 4.5 mm or less in width.

Figure 5:
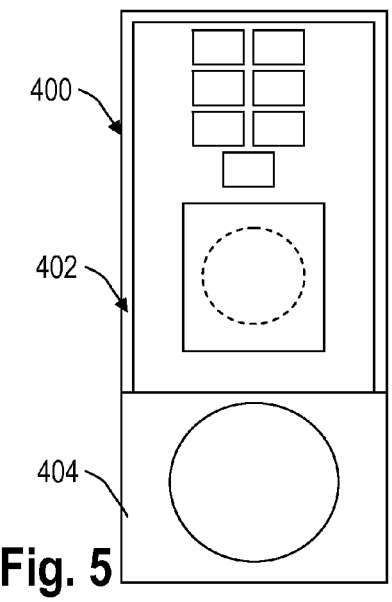

FIGS. 4 and 5 show a top view of a THA module 400 in accordance with various embodiments. The module 400 includes a THA 100 affixed to a frame 402. The frame 402 is similar to the frame 200, and further includes a handling feature 404 (i.e., a grip area) to facilitate handling by a user.

Figure 6A:
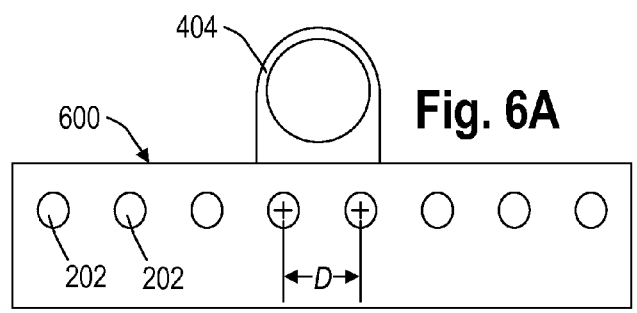
FIGS. 6A and 6B show a top views of frames configured to support one and two-dimensional arrays of head assemblies in accordance with various embodiments.

FIG. 6A shows a top view of a frame 600 configured to support a one-dimensional array of THAs 100 in accordance with various embodiments. The frame 600 is configured to support up to eight THAs 100. Other embodiments may be configured to support more or fewer THAs 100. For example, an embodiment of the frame may be configured to support up to 16 THAs 100. The frame 600 includes a handling feature 404. Some embodiments may omit the handling feature 404. The openings 202 may be spaced to in accordance with a desired droplet receptacle spacing. For example, in some embodiments the openings 202 may be spaced by an integer multiple of 2.25 mm to align with industry standard microplate well spacing. Some embodiments of the frame 600 are dimensioned (e.g., 1"×3") to allow manipulation by microscope slide robotics. Some embodiments of the frame 600 are dimensioned (e.g.; 3.5"× 5") to allow manipulation by microplate handling grippers and storage in microplate stacks and shelves.

Figure 6B:
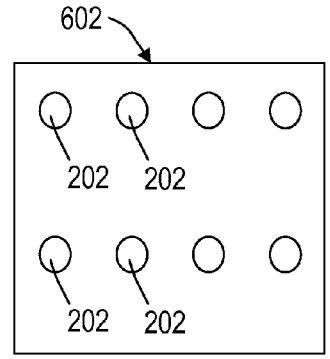

FIG. 6B shows a top view of a frame 602 configured to support a two-dimensional array of THAs 100 in accordance with various embodiments. The frame 602 is configured to support up to eight THAs 100. Other embodiments may be configured to support more (e.g., 16) or fewer THAs 100, by providing for a different number of rows and/or columns of THAs 100. The openings 202 may be spaced to in accordance with a desired droplet receptacle spacing (e.g., microplate well spacing, D=2.25 mm, D=4.5 mm, D=9 mm, etc). The frame 602 may be dimensioned to allow manipulation by microplate handling grippers and storage in microplate stacks and shelves.

Figure 7:
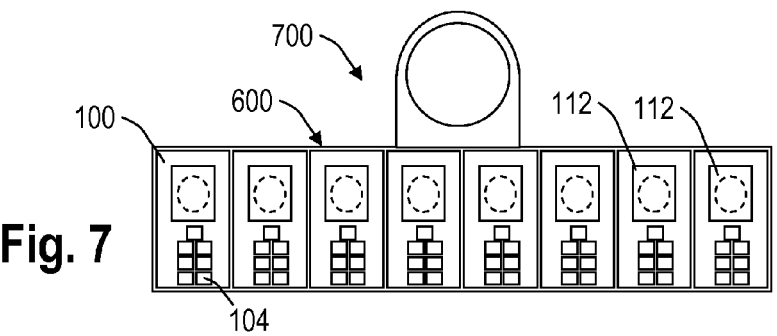
FIG. 7 shows a top view of a head assembly module including a one-dimensional array of head assemblies in accordance with various embodiments.

FIG. 7 shows a top view of a head assembly module 700 including a one-dimensional array of THAs 100 affixed to the frame 600 in accordance with various embodiments. Different liquids and/or different volumes of liquid may be loaded into different ones of the receptacles 112, and the THAs 100 of the module 700 may be dispensed from serially or in parallel to reduce microplate processing time. Electrical connections can be made to the electrical contact pads 104 one THA 100 at a time or to many or all THAs 100 simultaneously.

Figure 8:
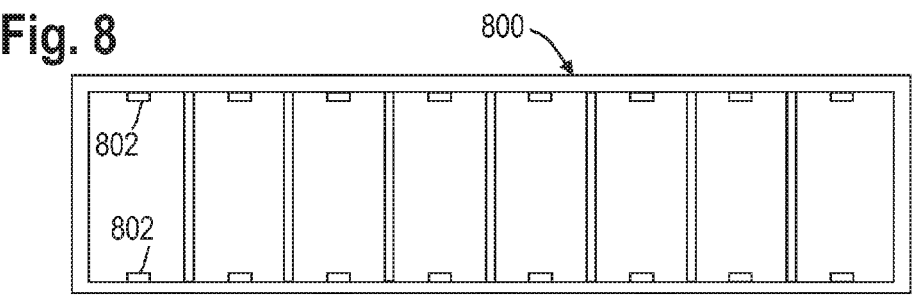
FIG. 8 shows a top view of a frame configured for user insertion of head assemblies in a one dimensional array in accordance with various embodiments.

FIG. 8 shows a top view of a carrier frame 800 configured for user insert on of head assembly modules 300 (or other one-dimensional modules, e.g., 1×2, 1×4, etc.) in a one-dimensional array in accordance with various embodiments. The carrier frame 800 allows for provision of a user selectable number of THA modules 300 to a dispensing instrument. The THAs 100 may snap into the carrier frame 800 using an alignment/retention feature 802 of the carrier frame 800 that cooperatively engages an associated feature of the module 300. The carrier frame 800 may be configured for handling by microscope slide robotics. Some embodiments of the carrier frame 800 are dimensioned to allow manipulation by microplate handling grippers and storage in microplate stacks and shelves. Some embodiments of the carrier frame 800 space the THA modules 300 in accordance with a desired drop receptacle spacing (e.g., an industry standard spacing, such as 9 mm, 4.5 mm, or 2.25 mm, or an integer multiple thereof).

Figure 9A:
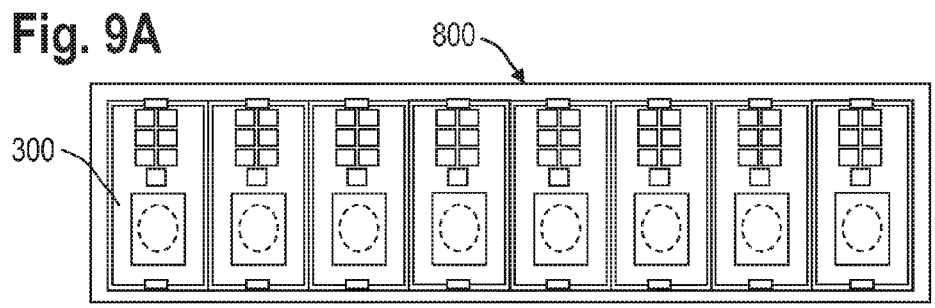
FIG. 9A shows a top view of a fully populated frame configured for user insertion of a head assemblies in a one dimensional array in accordance with various embodiments.
Figure 9B:
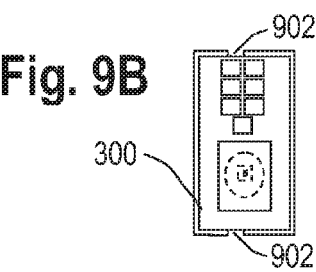
FIG. 9B shows a top view of a head assembly module that includes alignment/retention features in accordance with various embodiments.

FIG. 9A shows a top view of the carrier frame 800 fully populated with THA modules 300 in accordance with various embodiments. FIG. 9B shows a top vie of a THA module 300 that includes alignment/retention features 902. In some embodiments, friction between the alignment/retention features 802, 902 retains the THA module 300 in the carrier frame 800. In some embodiments, the carrier frame 800 extends no more than 2 millimeters below the printhead 106 to provide small printhead to drop receptacle spacing.

Figure 10:
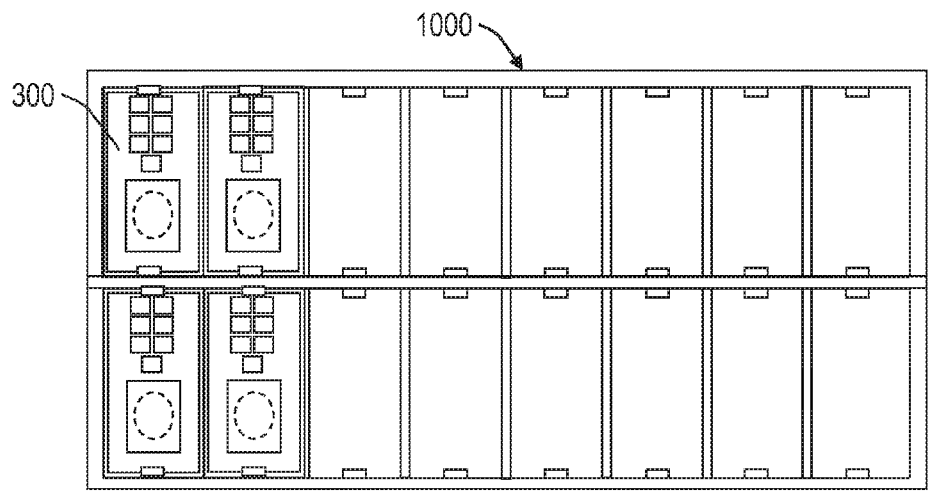
FIG. 10 shows a top view of a partially populated frame configured for user insertion of head assemblies in a two dimensional array in accordance with various embodiments.

FIG. 10 shows a top view of a partially populated carrier frame 1000 configured for user insertion of THA modules 300 (or other one or two-dimensional THA modules) in a two dimensional array in accordance with various embodiments. The carrier frame 1000 is configured to support up to 16 THA modules 300. A user may mount as many THA modules 300 as desired in the carrier frame 1000 at a time selected by the user (e.g., at time of use). Other embodiments of the carrier frame 1000 support more or fewer rows and/or columns of THA modules. The carrier frame 1000 may be configured for automated handling by microplate idling robotics.

FIGS. 11-15 show a bottom view of a THA module 300 including channels for light scattering drop detection ("LSDD") in accordance with various embodiments. Light scattering drop detection uses light scattered by a droplet passing through a light beam to detect the presence of the droplet. Performance of LSDD may be compromised when a THA 100 is mounted on a frame because the frame thickness increases the distance between the light beam and the surface of the printhead 106. To improve LSDD performance, embodiments of the frame 200, 400, 600, 800, 1000 include channels formed in the bottom side of the frame to reduce the distance between the light beam and the surface of the printhead 106. Channels also let the light beam pass through the frame without being reflected into a light collector. The channels also enable use of a higher numerical aperture light collector which allows for detection of more scattered light. Channel depth may range, for example, from 0.1 mm to 1.9 mm for a 2 mm frame (i.e., thickness of frame material above a channel may range from about 0.1 mm to about the frame thickness less 0.1 mm). A thicker frame may have a deeper channel in order to reduce spacing between the light beam and the surface of the printhead 106.

Figure 11:
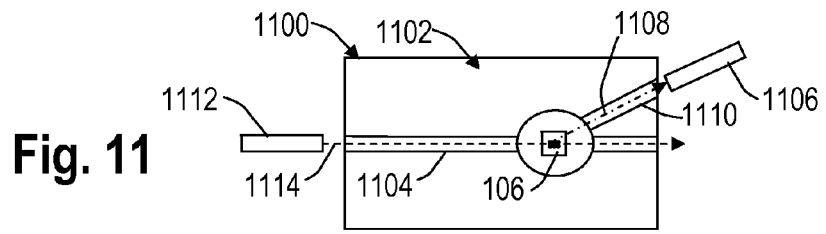
FIGS. 11-18 show a bottom view of a frame including channels for light scattering drop detection in accordance with various embodiments.

FIG. 11 shows a THA module 1100 including a frame 1102. The frame 1102 is similar to the frame 200 and includes channels (grooves) 1104 and 1110 provided in the bottom of the frame 1102. The channel 1104 allows light beam 1114 provided by light source 1112 to pass between the bottom surface of the frame 200 and the printhead 106, thereby reducing the distance between the beam 1114 and the printhead 106. As a droplet is discharged from the printhead 106 the beam 1114 intersects the droplet, and the droplet scatters the light beam 1114. Scattered light 1108 is collected by light collector 1106 via a channel 1108 formed in the bottom of the frame 200. In some embodiments, the light source 1112 is a laser light source (e.g., a laser diode), and the light collector 1106 is an optical fiber. The light collector 1106 provides light to a processing system that analyzes the collected light to identify droplets. Embodiments provide the channel 1110 at an angle of 15 degrees plus or minus 10 degrees from the channel 1104.

Figure 12:
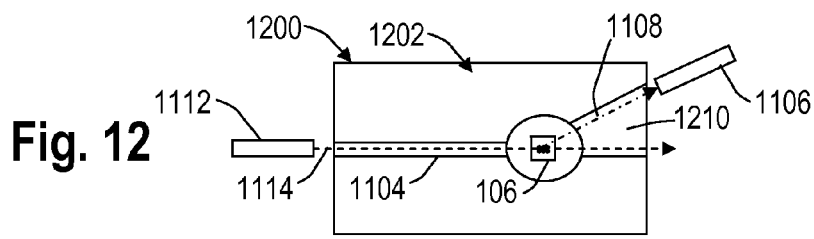

FIG. 12 shows a THA module 1200 including a frame 1202. The frame 1202 is similar to the frame 1102, but includes a triangular channel 1210 for collection of scattered light 1108. In some embodiments, the channel 1210 occupies an area extending from 0 degrees to 25 degrees from the channel 1104.

Figure 13:
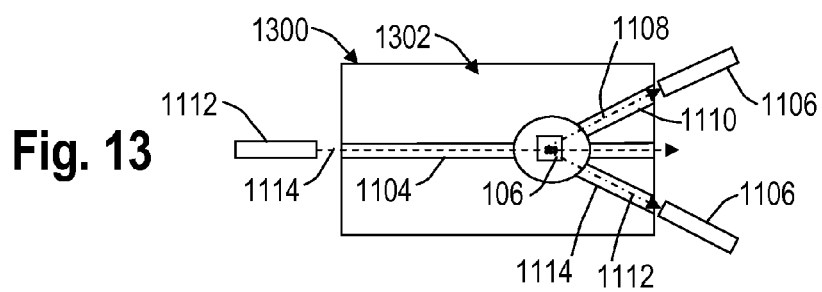

FIG. 13 shows a THA module 1300 including a frame 1302. The frame 1302 is similar to the frame 1102, but includes an additional channel 1114 for passage of scattered light 1112 for collection by a second instance of the light collector 1106. Embodiments provide the channel 1114 at an angle of 15 degrees plus or minus 10 degrees from the channel 1104.

Figure 14:
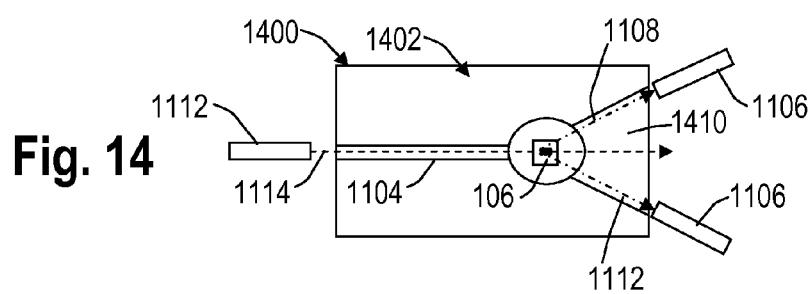

FIG. 14 shows a THA module 1400 including a frame 1402. The frame 1402 is similar to the frame 1202, but includes an enlarged triangular channel 1410. The channel 1410 provides passage for reception of scattered light 1108 and 1112 by light detectors. The channel 1410 allows capture of detected light at up to approximately a 25 degree angle from the light beam 1114.

Figure 15:
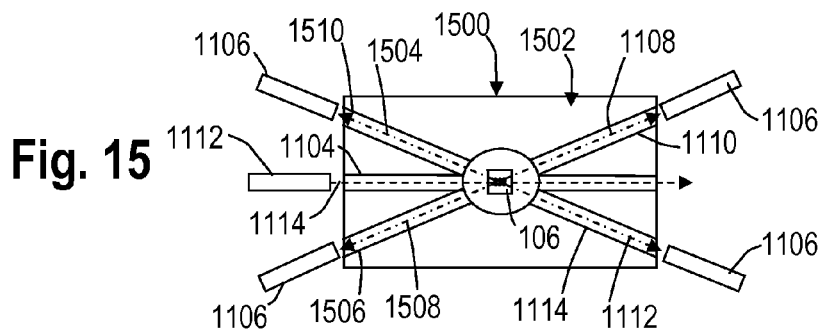

FIG. 15 shows a THA module 1500 including a frame 1502. The frame 1502 is similar to the frame 1302, but includes additional channels 1506 and 1510 for passage of back-scattered light 1508, 1504 for collection by light collectors 1106. Embodiments provide the channels 1506, 1510 at an angle of 15 degrees plus or minus 10 degrees from the channel 1104.

Figure 16:
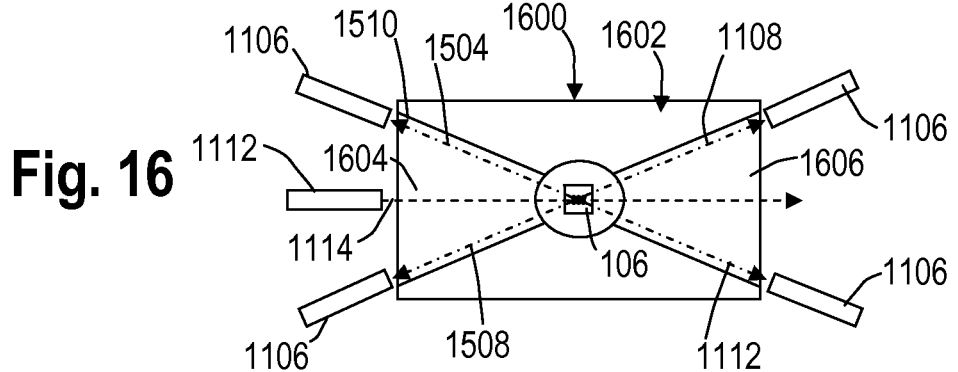

FIG. 16 shows a THA module 1600 including a frame 1602. The frame 1602 is similar to the frame 1502, but includes enlarged triangular channels 1604, 1606.

Figure 17:
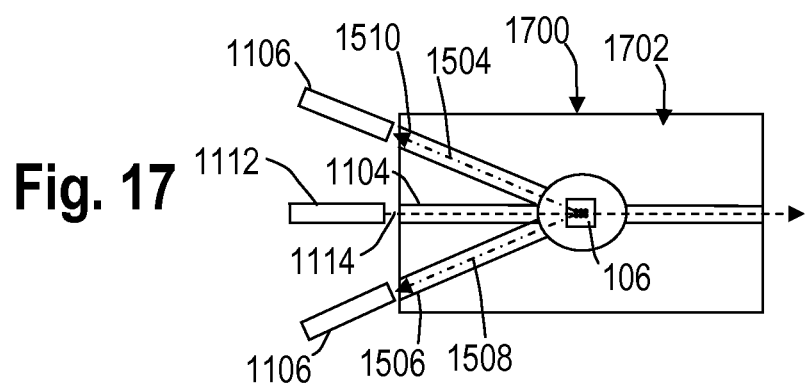

FIG. 17 shows a THA module 1700 including a frame 1702. The frame 1702 is similar to the frame 1502, but omits the channels 1110 and 1114. Thus, the frame 1702 is configured for collection of back-scattered light 1504, 1508.

Figure 18:
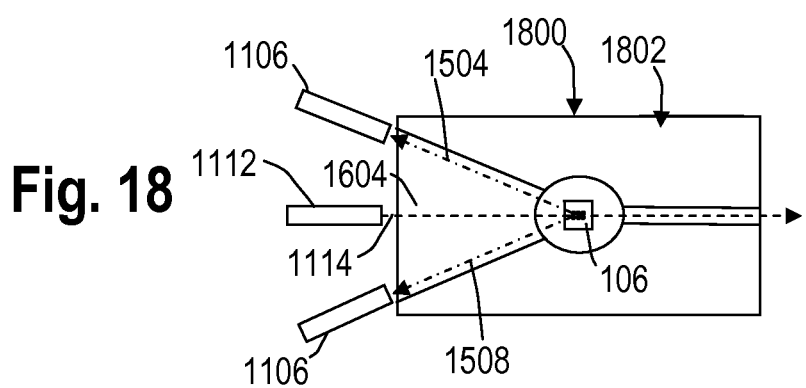

FIG. 18 shows a THA module 1800 including a frame 1802. The frame 1802 is similar to the frame 1702, but includes an enlarged triangular channel 1604. Thus, the frame 1802 is configured for collection of back-scattered light 1504, 1508.

Figure 19:
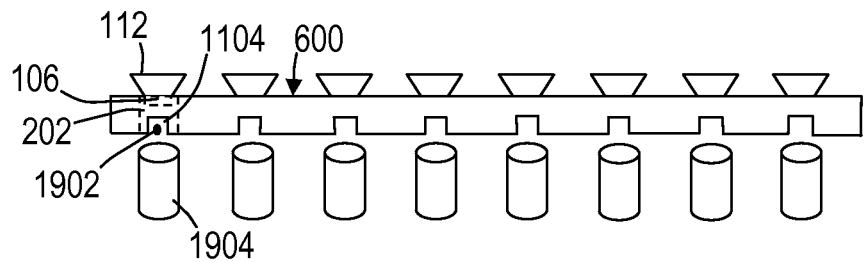
FIG. 19 shows a side view of a populated frame in accordance with various embodiments.

FIG. 19 shows a side view of a frame (e.g., frame 600 or frame 800) populated with THAs 100 in accordance with various embodiments. The printhead 106 is positioned in the opening 202 in the frame 600. Liquid is provided from the reservoir 112 to the printhead 106. The printhead 106 is activated to expel a droplet 1902 (e.g., a pico-liter droplet) that descends through the opening 202 in the frame 600 into a container 1904 located below the frame 600. The container 1604 may be a well of a microplate.

Figure 20:
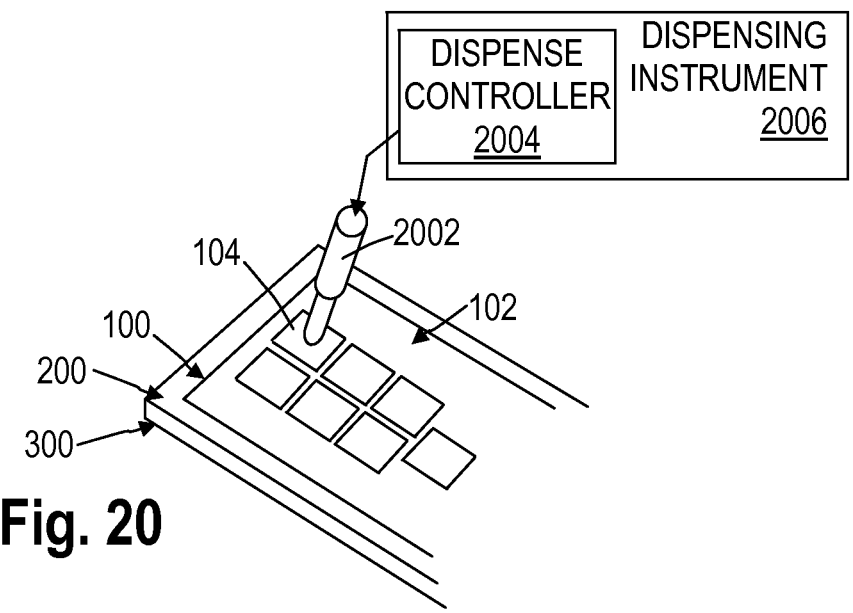
FIG. 20 shows a top view of a head assembly module with spring loaded pin connection in accordance with various embodiments.

FIG. 20 shows a top view of a THA module 300 with spring-loaded pin connection in accordance with various embodiments. The frame 200 provides support for the contact pads 104 allowing the spring-loaded pin 2002 to make an electrical connection with the pad 104 without deforming the flexible substrate 102 of the THA 100. Only a single spring-loaded pin 2002 is shown for purposes of illustration. In practice however, a spring-loaded pin 2002 may be provided for as many of the pads 104 as needed to provide power and control signals to the print head 106 from the dispense controller 2004 of a dispensing instrument 2006 with which the module 300 is used. Furthermore, spring-loaded pins 2002 may be provided for as many THAs 100 as are mounted on a module 700 and/or a user configurable carrier frame 800, 1000.

FIG. 21 shows a flow diagram for a method of titration in accordance with various embodiments. Though depicted sequentially as a matter of convenience, at least some of the actions shown can be performed in a different order and/or performed in parallel. Additionally, some embodiments may perform only some of the actions shown. At least some of the actions shown may be performed by logic of a dispensing instrument 2006. In some embodiments, such logic may include a processor executing software instructions stored in a computer readable medium.

In block 2102, a user affixes THA modules (e.g., THA module 300) to a carrier frame (e.g., carrier frame 800). The carrier frame 800 may support a one or two-dimensional array of modules. The number of THA modules 300 mounted to the carrier frame 800 is user selectable, and may be based, for example, on the number of wells to be processed, the number of different liquids to be dispensed, etc. The carrier frame 800 need not be fully populated.

In block 2104, the user installs the carrier frame 800 into the dispensing instrument 2006. The user may physically latch the carrier frame 800 into the instrument 2006 or the instrument 2006 may automatically position and latch the carrier frame 800.

In block 2106, the contact pads 104 of the modules 300 are electrically connected to the dispensing instrument 2006 via spring-loaded pins 2002. The dispensing instrument 2006 provides power and control signals to the printhead 106 via the electrical connections. In some embodiments, only a single module 300 at a time is electrically connected to the dispensing instrument 2006. In some embodiments, multiple modules 300 are individually/simultaneously connected to the dispensing instrument 2006. In such embodiments, the dispense controller 2004 can cause multiple modules 300 to dispense the same or different volumes of liquid in parallel.

In block 2108, the dispensing instrument 2006 electrically verifies some or all of the THAs on carrier frame 800. Electrical verification involves ensuring that the printhead is of the correct type and that it is electrically functional.

In block 2110 liquid is added to the reservoir 112 of one or more THA modules 300 mounted on the frame 800. In various embodiments, liquid may be added to the reservoir 112 before or after the carrier frame 800 is coupled to a dispensing instrument 2006. Different liquids may be loaded into different reservoirs 112, and different volumes of liquid may be added to different reservoirs 112. Reservoirs may be loaded at any time before the module 300 is used, including immediately prior to use. Liquid can be added to the reservoirs 112 manually or automatically and in serial or parallel fashion.

In block 2112, the dispensing instrument 2006 provides electrical signals that cause the modules 300 to discharge different numbers of droplets (e.g., pico-liter droplets) from printheads 106 of the modules 300. The different numbers of droplets form different concentrations of the liquid in the different containers 1604 (e.g., wells of a microplate) positioned beneath the carrier frame 800. Because some embodiments of the printhead 106 are capable of discharging a pico-liter droplet, serial dilution is not needed to provide a desired concentration of the liquid in the container 1604.

In block 2114, droplets discharged by the module 300 are detected using light scattering drop detection. A light source 1112 produces a light beam 1114 that propagates in a channel 1104 formed in the bottom surface of the module 300. The channel 1104 allows the light beam 1114 to pass closer to the printhead 106 that would be otherwise possible. The light beam 1114 is scattered as a droplet is discharged from the printhead 106 and passes through the beam 1114. The scattered light 1108 travels through a channel 1110 in the bottom surface of the module 300 to a light detector. The channel 1110 is provided at an angle of 5-25 degrees from the light beam 1114. The light detector provides the scattered light 1108 to a droplet detection system.

In block 2116, the dispensing instrument determines whether a desired number of droplets has been discharged. If the desired number of droplets has not been discharged, the dispensing instrument provides electrical signals that cause the modules to continue to discharge droplets. If the desired number of droplets has been discharged, the dispensing system stops droplet dispensing and performs the next operation.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A liquid dispensing device comprising:
    a carrier frame to retain a plurality of titration head assembly (THA) modules; and
    at least two THA modules, each THA module comprising;
        a titration head assembly comprising:
            an array of liquid droplet dispensers for dispensing individual liquid droplets;
            a corresponding array of electrical connections for driving said array of liquid droplet dispensers with a dispensing instrument separate from said THA module; and
            a reservoir on said THA module for receiving a supply of liquid and providing that liquid to said array of liquid droplet dispensers for dispensing; and
        a frame to support each titration head assembly, wherein the frame comprises:
            a plurality of lateral edges;
            an opening through which the individual liquid droplets pass; and
            an inlet channel formed in a bottom surface of said frame that extends from one lateral edge of said frame to said opening in said frame and an outlet channel that extends from the opening in the frame to another lateral edge of the frame, wherein the inlet channel and outlet channel are perpendicular to the opening in the frame;
        a light source;
        at least one light collector, wherein as the individual liquid droplets pass the inlet and outlet channels the droplet scatters light from the light source which is collected by the light collector via the inlet and outlet channels in the frame;
            said carrier frame comprising at least two places, each place being configured to support one of said at least two THA modules, each place comprising an opening through which said supported one of said at least two THA modules can dispense corresponding liquid droplets to containers positioned beneath the carrier frame.

2. The device of claim 1, wherein said carrier frame is rigid such that said carrier frame supports said at least two THA modules as said device, including said carrier frame and said at least two THA modules, is installed into a dispensing instrument.

3. The device of claim 2, wherein said frame further comprises a handle feature with a grip area with a handle feature having a different geometry than a remainder of a frame perimeter.

4. The device of claim 1, wherein said at least two THA modules are releasably received and supported on said carrier frame and electrical contacts for connecting said THA modules to the dispensing instrument are disposed on surface opposite a dispensing port.

5. The device of claim 1, wherein said openings in the frame are aligned with industry standard microplate well spacing.

6. The device of claim 5, wherein said openings in said frames are spaced by an integer multiple of 2.25 mm to align with said industry standard microplate well spacing.

7. The device of claim 1, wherein said carrier frame is sized to support at least eight THA modules.

8. The device of claim 1, wherein said carrier frame is sized to support up to eight THA modules.

9. The device of claim 1 wherein a number frames are stackable.

10. The device of claim 1 wherein said frame further comprises machine readable identification marks.

11. The device of claim 1, wherein said at least two THA modules include different reservoirs to hold different volumes of fluid.

12. The device of claim 1, wherein a bottom surface of said frame is less than 2 millimeters below said array of liquid droplet dispensers.

13. A titration system comprising the device of claim 1:
wherein said dispensing instrument is for providing electrical signals via said electrical connections to drive said array of liquid droplet dispensers to dispense droplets of at least two different liquids, each of said at least two THA modules dispensing a different liquid, such that different concentrations of one of the two liquids in the other are dispensed by said liquid droplet dispensers into separate containers positioned beneath said carrier frame.

14. The system of claim 13, wherein said dispensing instrument is configured to hold fluid in a pico-liter range to produce said different concentrations of liquid in said separate containers without using subsequent dilution of contents of any said separate container.

15. The system of claim 13, wherein said each of said at least two THA modules comprises a flexible substrate for supporting said array of liquid droplet dispensers, electric connections and containers.

16. The system of claim 13, wherein said electrical connections comprise exposed pads for making an electrical connection with a spring-loaded pin of said dispensing instrument.

17. The system of claim 13, wherein said at least two THA modules snap into said carrier frame using a retention feature of the carrier frame that cooperatively engages an associated retention feature of said at least two THA modules.

* * * * *

UNITED STATES PATENT AND TRADEMARK OFFICE
CERTIFICATE OF CORRECTION

PATENT NO. : 9,433,939 B2  
APPLICATION NO. : 12/870546  
DATED : September 6, 2016  
INVENTOR(S) : Christie Dudenhoefer et al.

Page 1 of 1

It is certified that error appears in the above-identified patent and that said Letters Patent is hereby corrected as shown below:

In Column 9, Line 4, in Claim 4, delete "on" and insert -- on a --, therefor.

Signed and Sealed this  
Seventeenth Day of January, 2017

Michelle K. Lee  
*Director of the United States Patent and Trademark Office*